US012679964B2

(12) United States Patent
Kraft et al.

(10) Patent No.: US 12,679,964 B2
(45) Date of Patent: Jul. 14, 2026

(54) TETRAISOPENTYL ESTERS OF BUTANETETRACARBOXYLIC ACID, PRODUCTION THEREOF AND USE THEREOF AS PLASTICIZERS

(71) Applicant: Evonik Oxeno GmbH & Co. KG, Marl (DE)

(72) Inventors: Johannes Kraft, Offenbach (DE); Imke Schulz, Leudinghausen (DE); Michael Grass, Haltern am See (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 498 days.

(21) Appl. No.: 18/476,537

(22) Filed: Sep. 28, 2023

(65) Prior Publication Data

US 2024/0110050 A1 Apr. 4, 2024

(30) Foreign Application Priority Data

Sep. 30, 2022 (EP) ..................................... 22199108

(51) Int. Cl.
*C07C 67/02* (2006.01)
*C07C 67/08* (2006.01)
*C08L 27/06* (2006.01)

(52) U.S. Cl.
CPC .............. *C08L 27/06* (2013.01); *C07C 67/02* (2013.01); *C07C 67/08* (2013.01); *C08L 2666/34* (2013.01); *C08L 2666/68* (2013.01)

(58) Field of Classification Search
CPC ......... C07C 67/02; C07C 67/08; C08L 27/06; C08L 2666/34; C08L 2666/68
USPC ....................................................... 524/285
See application file for complete search history.

(56) References Cited

U.S. PATENT DOCUMENTS

2011/0257317 A1* 10/2011 Baugh ...................... C08K 5/12
524/308

FOREIGN PATENT DOCUMENTS

JP       S5922950       2/1984
JP       H0598106       4/1993
JP       H0598106 A   *   4/1993

OTHER PUBLICATIONS

Schulz et al., U.S. Appl. No. 18/476,766, filed Sep. 28, 2023.
Schulz et al., U.S. Appl. No. 18/476,901, filed Sep. 28, 2023.
European Search Report dated Feb. 9, 2024, in European Application No. 23195912.3, 8 pages.
Database CA [Online], Chemical Abstracts Service, Columbus Ohio, US, Sep. 15, 1984, "Poly (vinyl chloride) resin compositions", XP002808623, Stn Database accession No. 1984:492123 & JPS5922950A (Chisso Corp) Feb. 6, 1984, 3 pages.
Database CA [Online], Chemical Abstracts Service, Columbus Ohio, US, Feb. 5, 1994, Fujitani Yoshifumi et al. "Halogen-containing polymer compositions with high usable temperature", XP002808624, in STN Database accession No. 1994:55944 & JPH0598106A (New Japan Chem Co Ltd) Apr. 20, 1993, 3 pages.
European Search Report dated Mar. 1, 2023, in European Application No. 22199108.6, 7 pages.

* cited by examiner

*Primary Examiner* — Kelechi C Egwim
(74) *Attorney, Agent, or Firm* — Grüneberg Global IP, PLLC

(57) ABSTRACT

Tetraisopentyl esters of butanetetracarboxylic acid are useful as plasticizers or as part of a plasticizer composition for polymers. A process for the production thereof, plasticizer compositions containing the tetraisopentyl esters of butanetetracarboxylic acid, and plastics compositions containing the tetraisopentyl esters of butanetetracarboxylic acid are also provided.

18 Claims, 1 Drawing Sheet

TETRAISOPENTYL ESTERS OF BUTANETETRACARBOXYLIC ACID, PRODUCTION THEREOF AND USE THEREOF AS PLASTICIZERS

CROSS-REFERENCE TO RELATED APPLICATIONS

This application claims priority to European Application No. 22199108.6, filed on Sep. 30, 2022, the content of which is hereby incorporated by reference in its entirety.

BACKGROUND OF THE INVENTION

Field of the Invention

The present invention relates to tetraisopentyl esters of butanetetracarboxylic acid, to the production thereof and to the use thereof as plasticizers or as part of a plasticizer composition for polymers. Also disclosed are plasticizer compositions containing the tetraisopentyl esters of butanetetracarboxylic acid and plastics compositions containing the tetraisopentyl esters of butanetetracarboxylic acid.

Description of Related Art

In many fields of application plastics/polymers are admixed with plasticizers or plasticizer compositions to improve processability and/or to adapt application-relevant properties. Due to their advantageous properties, compounds from the group of phthalates, in particular diethylhexyl phthalate (DEHP), diisononyl phthalate (DINP) and diisodecyl phthalate (DIDP), still remain among the most important plasticizers for plastics/polymers, especially for PVC and vinyl chloride-containing copolymers. Due to discourse about possible toxicological effects of this class of substances, alternatives for phthalate-based plasticizers have been sought for many years.

Various compounds are discussed as alternative plasticizers, these including inter alfa alkyl esters of butanetetracarboxylic acid which are already known to those skilled in the art from US 2011/0257317 A1 for example. The alkyl esters of butanetetracarboxylic acid disclosed therein have a maximum proportion of alkyl radicals branched at the beta position of 40%.

SUMMARY OF THE INVENTION

Having regard to tetraisopentyl esters of butanetetracarboxylic acid it has now been found that, surprisingly, improved properties occur at a certain molar proportion of 2-methylbutyl radicals based on the total isomeric pentyl radicals. The underlying problem addressed by the present invention was accordingly that of providing tetraisopentyl esters of butanetetracarboxylic acid with improved properties.

The underlying problem is solved by the mixture of tetraisopentyl esters of 1,2,3,4-butanetetracarboxylic acid according to the description below. Preferred embodiments are also specified below.

BRIEF DESCRIPTION OF THE DRAWING

The FIGURE shows numbering of the carbon atoms in the different pentyl radicals.

DETAILED DESCRIPTION OF THE INVENTION

In the context of the present invention, the terms "isopentyl", "isopentyl radicals" or the like are used. This emphasizes that the esters according to the invention contain various pentyl isomers, in particular 2-methylbutyl and/or 3-methylbutyl and/or n-pentyl. The terms "isopentyl", "isopentyl radicals" or the like are therefore to be understood as being synonymous with the term "pentyl" and do not refer to a single specific C5-alkyl group.

The present invention accordingly relates to a mixture of tetraisopentyl esters of 1,2,3,4-butanetetracarboxylic acid, wherein 45 to 60 mol % of the isopentyl radicals in the mixture are 2-methylbutyl radicals. The reported percentages in each case refer to the total isopentyl radicals in the mixture. A preferred embodiment of the present invention provides that in the mixture of tetraisopentyl esters of 1,2,3,4-butanetetracarboxylic acid 50 to 60 mol % of the isopentyl radicals in the mixture are 2-methylbutyl radicals.

The remaining isopentyl radicals in the inventive mixture of tetraisopentyl esters of 1,2,3,4-butanetetracarboxylic acid are preferably n-pentyl radicals or 3-methylbutyl radicals, in particular 40 to 55 mol % of the isopentyl radicals in the inventive mixture are n-pentyl radicals, 3-methylbutyl radicals or a mixture of n-pentyl radicals and 3-methylbutyl radicals. A preferred embodiment of the present invention provides that in the mixture of tetraisopentyl esters of 1,2,3,4-butanetetracarboxylic acid 40 to 50 mol % of the isopentyl radicals are n-pentyl radicals, 3-methylbutyl radicals or a mixture of n-pentyl radicals and 3-methylbutyl radicals. A preferred embodiment of the present invention provides that in the inventive mixture of tetraisopentyl esters of 1,2,3,4-butanetetracarboxylic acid 0 to 4 mol %, preferably 0 to 2 mol %, particularly preferably 0-1 mol % of the isopentyl radicals are 3-methylbutyl radicals.

The inventive mixture of tetraisopentyl esters of 1,2,3,4-butanetetracarboxylic acid may be produced by esterification of the 1,2,3,4-butanetetracarboxylic acid with a suitable isopentanol mixture. In this context isopentanol mixture is to be understood as meaning that this mixture contains at least 2-methylbutanol and n-pentanol and/or 3-methylbutanol. It should understandably be ensured during the esterification that the mixture contains sufficient 2-methylbutanol to obtain the required amount of 2-methylbutyl radicals in the ester formed. As is well known the selection of suitable isopentanol mixtures may be effected by reaction and analysis of the esters formed.

The esterification is preferably carried out in the presence of a catalyst. Known catalyst systems suitable for esterification may in principle be used to this end. Suitable catalysts for the esterification to produce the inventive tetraisopentyl esters of 1,2,3,4-butanetetracarboxylic acid are titanate catalysts, for example tetra-n-butyl titanate, zirconates or sulfonic acids.

The esterification to produce the esters according to the invention is preferably carried out at a temperature of 120° C. to 250° C., more preferably at a temperature of 140° C. to 230° C., particularly preferably at a temperature of 160° C. to 215° C. The pressure during the esterification should preferably not be excessively high since this would increase the boiling temperature and thus also the esterification temperature. The pressure during the esterification is therefore 3 bar absolute or less, particularly preferably not less than 0.5 bar absolute.

During an esterification the reaction of the acid group with an alcohol forms water. This water is also called water of reaction. In a preferred embodiment of the present invention at least a portion of the water of reaction formed is separated during the ongoing reaction. This can inter alia shift the equilibrium of the reaction in the right direction.

The progress of the esterification reaction can be monitored by monitoring a parameter. The acid number or the amount of water may be monitored for example. Monitoring by gas chromatography, where the proportion of reactants and/or products may be determined, is also possible.

Once the reaction has progressed to a sufficient extent the reaction may be terminated. This may be done for example by addition of a base, for example aqueous sodium hydroxide solution. This generally destroys the catalyst. A person skilled in the art is well aware of this. The reaction solution may subsequently be worked up with known processes, for example by thermal separation.

The inventive mixture of tetraisopentyl esters of 1,2,3,4-butanetetracarboxylic acid may also be produced by transesterification of the tetramethyl ester of 1,2,3,4-butanetetracarboxylic acid with a suitable isopentanol mixture. In the present context isopentanol mixture is to be understood as meaning that this mixture contains at least 2-methylbutanol and n-pentanol and/or 3-methylbutanol. It should understandably be ensured during the esterification that the mixture contains sufficient 2-methylbutanol to obtain the required amount of 2-methylbutyl radicals in the ester formed. As is well known the selection of suitable isopentanol mixtures may be effected by reaction and analysis of the esters formed. The progress of the transesterification reaction may be monitored by monitoring a parameter. Only monitoring by gas chromatography, where the proportion of reactants and/or products may be determined, is possible here.

The inventive mixture of tetraisopentyl esters of 1,2,3,4-butanetetracarboxylic acid has advantageous properties when used as a plasticizer for polymers. A further subject of the present invention is therefore the use of the mixture of tetraisopentyl esters of 1,2,3,4-butanetetracarboxylic acid as a plasticizer for polymers. Suitable polymers are specified below, preference being given to PVC or vinyl chloride-containing copolymers.

A further subject of the present invention is a plasticizer composition which contains a further plasticizer in addition to the mixture of tetraisopentyl esters of 1,2,3,4-butanetetracarboxylic acid. Depending on the intended application, the plasticizer composition may contain one or more additional plasticizers that are especially distinct from the inventive mixture of tetraisopentyl esters of 1,2,3,4-butanetetracarboxylic acid to specifically adjust the properties of the resulting plasticizer composition. However, in a particularly preferred embodiment the plasticizer composition comprises less than 5% by weight, more preferably less than 0.5% by weight, particularly preferably less than 0.1% by weight, of phthalates.

The additional plasticizers in the inventive plasticizer composition may be selected from the group consisting of adipates, benzoates, for example monobenzoates or glycol dibenzoates, chlorinated hydrocarbons (so-called chloroparaffins), citrates, cyclohexanedicarboxylates, epoxidized fatty acid esters, epoxidized vegetable oils, epoxidized acylated glycerides, furandicarboxylates, phosphates, succinates, sulfonamides, sulfonates, terephthalates, isophthalates, trimellitates and oligomeric or polymeric esters based on adipic acid, succinic acid or sebacic acid. In a preferred embodiment of the present invention, the plasticizer composition comprises a further plasticizer selected from the group consisting of alkyl benzoates, alkylsulfonic esters of phenol, dialkyl adipates, glycerol esters, C4-C6-acids of polyols, trialkyl citrates, acetylated trialkyl citrates, glycol dibenzoates, trialkyl esters of trimellitic acid, dialkyl terephthalates, dialkyl phthalates, dialkyl isophthalates, esters of furandicarboxylic acid, dialkanoyl esters of dianhydrohexitols (for example isosorbide), epoxidized fatty acid alkyl esters, polymer plasticizers, for example polyadipates, and dialkyl esters of 1,2-, 1,3- or 1,4-cyclohexandicarboxylic acid.

In a further preferred embodiment the further plasticizer present in the plasticizer composition is selected from the group consisting of C8- to C13-alkyl benzoates, C4- to C10-dialkyl adipates, pentaerythritol tetravalerate, acetylated trialkyl citrates having C4 to C9-alkyl groups, C4- to C10-trialkyl trimellitates, C4- to C9-dialkyl terephthalates, C4- to C13-dialkyl phthalates, especially C9- to C13-dialkyl phthalates and C4- to C10-dialkyl esters of 1,2-, 1,3- or 1,4-cyclohexanedicarboxylic acid.

A further subject of the present invention is therefore a plastics composition containing the inventive mixture of tetraisopentyl esters of 1,2,3,4-butanetetracarboxylic acid or the plasticizer composition and one or more polymers.

Suitable polymers are preferably selected from the group consisting of PVC, homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atom(s), acrylonitrile or cyclic olefins, polyvinylidene chloride (PVDC), polyacrylates, in particular polymethyl methacrylate (PMMA), poly-alkyl methacrylate (PAMA), polyureas, silylated polymers, fluoropolymers, especially polyvinylidene fluoride (PVDF), polytetrafluoroethylene (PTFE), polyvinyl acetate (PVAc), polyvinyl alcohol (PVA), polyvinyl acetals, especially poly-vinyl butyral (PVB), polystyrene polymers, especially polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPO), polyethylene-vinyl acetate (EVA), polycarbonates, polyethylene terephthalate (PET), polybutylene terephthalate (PST), polyoxymethylene (POM), polyimide (PA), polyethylene glycol (PEG), polyurethane (PU), thermoplastic polyurethane (TPU), polysulfides (PSu), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAE), rubber and silicones.

In a preferred embodiment at least one polymer or preferably at least 90% by weight of the two or more polymers in the plasticizer composition is/are selected from the group consisting of polyvinyl chloride (PVC), polyalkyl methacrylate (PAMA), polyvinyl butyral (PVB), polyurethane, polysulfide, polylactic acid (PLA), polyhydroxybutyral (PHB), nitrocellulose and copolymers of vinyl chloride with vinyl acetate or with butyl acrylate. PVC is particularly preferred.

The amount of the inventive mixture of tetraisopentyl esters of 1,2,3,4-butanetetracarboxylic acid or of the plasticizer composition in the plastics composition is preferably 5 to 150 parts by mass, preferably 10 to 120 parts by mass, particularly preferably 15 to 110 parts by mass and very particularly preferably 20 to 100 parts by mass per 100 parts by mass of polymer. Also conceivable however are compositions containing one or more polymers which comprise less than 20 parts by mass of the inventive tetraisopentyl esters of 1,2,3,4-butanetetracarboxylic acid per 100 parts by mass of the polymer.

Specific compositions/mixtures of plasticizers comprising the inventive mixtures of tetraisopentyl esters of 1,2,3,4-butanetetracarboxylic acid that are preferred in the context of the present invention are reported below.

A preferred subject of the present invention is a plastics composition comprising the mixture of tetraisopentyl esters of 1,2,3,4-butanetetracarboxylic acid and diethylhexyl terephthalate (DEHT or DOTP) and at least one polymer, preferably PVC.

A further preferred subject of the present invention is a plastics composition comprising the mixture of tetraisopentyl esters of 1,2,3,4-butanetetracarboxylic acid and 1,2- or 1,4-cyclohexanedicarboxylic esters, in particular the corresponding diisononyl or di-2-ethylhexyl esters, and at least one polymer, preferably PVC.

Also preferred is a plastics composition comprising the mixture of tetraisopentyl esters of 1,2,3,4-butanetetracarboxylic acid and trialkyl esters of trimellitic acid in which the alkyl radicals comprise 4 or more carbon atoms, preferably 5, 8, 9 or 10 carbon atoms, and at least one polymer, preferably PVC.

Also preferred is a plastics composition comprising the mixture of tetraisopentyl esters of 1,2,3,4-butanetetracarboxylic acid and trialkyl esters of 1,2,4-cyclohexanetricarboxylic acid in which the alkyl radicals comprise 4 or more carbon atoms, preferably 5, 8, 9 or 10 carbon atoms, and at least one polymer, preferably PVC.

A further preferred subject of the present invention is a plastics composition containing the mixture of tetraisopentyl esters of 1,2,3,4-butanetetracarboxylic acid and a rapidly gelating plasticizer selected from the group consisting of dibutyl terephthalate, di(iso)-pentyl terephthalate, isodecyl benzoate, isononyl benzoate, acetyltributyl citrate, tributyl citrate, dipropylene glycol dibenzoate, diethylene glycol dibenzoate, triethylene glycol dibenzoate and mixtures of two or more thereof, and at least one polymer, preferably PVC.

The inventive plastics composition is preferably a constituent of an adhesive, of a sealing composition, of a coating composition, of a lacquer, of a paint, of a plastisol, of a dryblend, of a foam, of a synthetic leather, of a floor covering, particularly the topcoat or foam layer thereof, of a roofing membrane, of an underbody protection, of a fabric coating, of a cable, of a wire insulation, of a hose, of an extruded article, of a film, of an article in the field of automotive interiors, of a wallpaper, of an ink, of a toy, of a contact sheet, of a foodstuffs packaging or of a medical article, especially of a tube or of a blood bag.

A further subject of the present invention is therefore the use of the plastics composition in adhesives, sealing compositions, coating compositions, lacquers, paints, plastisols, foams, synthetic leathers, floor coverings, particularly the topcoat or foam layer, roofing membranes, underbody protection, fabric coatings, cables, wire insulation, hoses, extruded articles, films, in the field of automotive interiors, in wallpapers, inks, toys, contact sheets, foodstuffs packaging or medical articles, especially in tubes or blood bags.

It has already been mentioned that the terms "isopentyl", "isopentyl radicals" or the like are to be understood as being synonymous with the term "pentyl" and do not refer to a single specific C5-alkyl group. In this respect, the individual inventive subjects of the present invention could also be described as follows:

1. Mixture of tetrapentyl esters of 1,2,3,4-butanetetracarboxylic acid, wherein 45 to 60 mol % of the isopentyl radicals in the mixture are 2-methylbutyl radicals.

2. Mixture according to subject 1, wherein 50 to 60 mol % of the pentyl radicals in the mixture are 2-methylbutyl radicals.

3. Mixture according to subject 1, wherein 40 to 55 mol % of the pentyl radicals in the mixture are n-pentyl radicals, 3-methylbutyl radicals or a mixture of n-pentyl radicals and 3-methylbutyl radicals.

4. Mixture according to subject 2, wherein 40 to 50 mol % of the pentyl radicals in the mixture are n-pentyl radicals, 3-methylbutyl radicals or a mixture of n-pentyl radicals and 3-methylbutyl radicals.

5. Process for producing the mixture of tetrapentyl esters of 1,2,3,4-butanetetracarboxylic acid according to any of subjects 1 to 4, wherein the producing is carried out either by esterification of 1,2,3,4-butanetetracarboxylic acid with a pentanol mixture or by transesterification of the tetramethyl ester of 1,2,3,4-butanetetracarboxylic acid with a pentanol mixture.

6. Process according to subject 5, wherein the water of reaction formed during the esterification is separated during the reaction.

7. Process according to subject 5 or 6, wherein the esterification is performed at a temperature in the range from 120° C. to 250° C.

8. Use of the mixture of tetrapentyl esters of 1,2,3,4-butanetetracarboxylic acid according to any of subjects 1 to 4 as a plasticizer for polymers, in particular for PVC or vinyl chloride-containing copolymers.

9. Plasticizer composition containing the mixture of tetrapentyl esters of 1,2,3,4-butanetetracarboxylic acid according to any of subjects 1 to 4 and at least one further plasticizing compound.

10. Plasticizer composition according to subject 9, wherein the further plasticizing compound is selected from the group consisting of adipates, benzoates, for example monobenzoates or glycol dibenzoates, chlorinated hydrocarbons (so-called chloroparaffins), citrates, cyclohexanedicarboxylates, epoxidized fatty acid esters, epoxidized vegetable oils, epoxidized acylated glycerides, furandicarboxylates, phosphates, succinates, sulfonamides, sulfonates, terephthalates, trimellitates and oligomeric or polymeric esters based on adipic acid, succinic acid or sebacic acid.

11. Plasticizer composition according to subject 9 or 10, wherein the plasticizer composition contains less than 5% by weight, more preferably less than 0.5% by weight, particularly preferably less than 0.1% by weight, of phthalates.

12. Plastics composition containing the mixture of tetrapentyl esters of 1,2,3,4-butanetetracarboxylic acid according to any of subjects 1 to 4 or the plasticizer composition according to any of subjects 9 to 11 and one or more polymers.

13. Plastics composition according to subject 12, wherein the one or more polymers are selected from the group consisting of PVC, homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atom(s), acrylonitrile or cyclic olefins, polyvinylidene chloride (PVDC), polyacrylates, in particular polymethyl methacrylate (PMMA), polyalkyl methacrylate (PAMA), polyureas, silylated polymers, fluoropolymers, especially polyvinylidene fluoride (PVDF), polytetrafluoroethylene (PTFE), polyvinyl acetate (PVAc), polyvinyl alcohol (PVA), polyvinyl acetals, especially polyvinyl butyral (PVB), polystyrene polymers, especially polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, especially polyethylene (PE) or polypropylene (PP), thermoplastic polyolefins (TPG), polyethylene-vinyl acetate (EVA), polycarbonates, polyethylene terephthalate (PET), polybutylene terephthalate (PBT), polyoxymethylene (POW polyamide (PA), polyethylene glycol (PEG), polyurethane (PU), thermoplastic polyurethane (TPU), polysulfides (PStr), biopolymers, especially polylactic acid (PLA), polyhydroxybutyral (PHB), polyhydroxyvaleric acid (PHV), polyesters, starch, cellulose and cellulose derivatives, especially nitrocellulose (NC), ethylcellulose (EC), cellulose acetate (CA), cellulose acetate/butyrate (CAB), rubber and silicones.

14. Plastics composition according to subject 12 or 13, wherein the amount of the inventive mixture of tetrapentyl esters of 1,2,3,4-butanetetracarboxylic acid or the plasticizer composition in the plastics composition is 5 to 150 parts by mass, preferably 10 to 120 parts by mass and particularly preferably 15 to 110 parts by mass per 100 parts by mass of polymer.

15. Use of the plastics composition according to any of subjects 12 to 14 in adhesives, sealing compositions, coating compositions, lacquers, paints, plastisols, foams, synthetic leathers, floor coverings (for example the topcoat), roofing membranes, underbody protection, fabric coatings, cables, wire insulation, hoses, extruded articles, films, in the field of automotive interiors, in wallpapers, inks, toys, contact sheets, foodstuffs packaging or medical articles, for example tubes or blood bags.

The invention is elucidated hereinbelow by reference to examples. The examples are intended to be illustrative and are not to be understood as being limiting.

EXAMPLES

Synthesis of the mixture of tetraisopentyl esters of 1,2,3,4-butanetetracarboxylic acid An apparatus was charged with 5 mol of 1,2,3,4-butanetetracarboxylic acid (Alfa Aesar, purity: >98%) and corresponding quantities of the alcohols 2-methylbutanol, n-pentanol and 3-methylbutanol (2-methylbutanol; Sigma Aldrich, purity ≥99%; 3-methylbutanol: Honeywell, purity ≥98.5%; n-pentanol: Honeywell, purity ≥99%). 3.4 g of tetra-n-butyl titanate (0.01 mol, Sigma Aldrich, purity: >97%) were added thereto as catalyst and the reaction was commenced. The reaction was carried out with nitrogen sparging. The reactants were slowly heated to a reaction temperature of 200° C. Once the reaction temperature had been reached additional alcohol was metered in. It was ensured during metered addition that the reaction temperature did not fall below 200° C.

In the course of the esterification, 360 ml of water was produced (20 mol of water of reaction). The water formed during the reaction was continuously removed via a water trap. Once 360 ml of water of reaction had been formed the acid number (AN) was determined using a sample from the reaction. Reaction progress was monitored at regular intervals via the AN until an AN of <0.5 mg of KOH per g sample was achieved. The batch was then cooled and the catalyst destroyed by addition of aqueous sodium hydroxide solution.

The reaction output from the esterification was transferred into a stirred flask fitted with a stirrer. The equipment was purged with nitrogen (6 l/h). Under vacuum (about 1-5 mbar), the reaction output was slowly heated and the temperature increased to 163° C. After complete distillation of the excess alcohol the product was cooled to 80° C. and filtered. The filtrate was subjected to NMR analysis to determine the composition of the ester radicals in the product.

NMR Analysis

The composition of the tetraisopentyl-1,2,3,4-butanetetracarboxylic esters, i.e. the respective proportion of the different isomeric butyl radicals based on the entirety of all butyl radicals, may be determined for example by $^1$H-NMR and $^{13}$C-NMR spectroscopy. Due to its higher accuracy, determination of the composition was here performed using $^1$H-NMR spectroscopy on a solution of the tetraisopentyl-1,2,3,4-butanetetracarboxylic ester mixtures in deuterochloroform ($CDCl_3$). To record the 1H-NMR spectra about 20 mg of substance were dissolved in about 0.6 ml of $CDCl_3$ (in each case containing about 1% by mass of TMS) and filled into an NMR tube having a diameter of 5 mm. The $CDCl_3$ used was first dried over a molecular sieve to prevent corruption of the measured values by any water present.

The NMR spectroscopy analyses may in principle be carried out using any commercially available NMR instrument. For the present NMR spectroscopy analyses a Bruker Avance 500 instrument was used. The $^1$H-NMR spectra were recorded at a temperature of 300 K with a delay of d1=5 seconds, 32 scans, a pulse length of about 12 μs (30° excitation pulse) and a sweep width of 10 000 Hz with a 5 mm Prodigy Cryo sample head (CPPBO) with Bruker Cooling Unit (BCU 05). The resonance signals were recorded relative to the chemical shifts of tetramethylsilane (TMS=0 ppm) as internal standard. Other commercial NMR instruments give comparable results with the same operating parameters.

The FIGURE is merely to aid comprehension of the elucidated method of determination. Relevant here is the assigned numbering of the carbon atoms of the methyl groups and the methylene groups adjacent to the oxygen atom in each case in an n-pentyl radical ($C14H_3$ and $C10H_2$), in a 2-methylbutyl radical ($C23H_3$, $C24H_3$ and $C20H_2$) and in a 3-methylbutyl radical ($C33H_3$ and $C30H_2$).

The FIGURE shows numbering of the carbon atoms in the different pentyl radicals. In the structure of the FIGURE, each R=n-pentanol, 2-methylbutanol or 3-methylbutanol.

The obtained $^1$H-NMR spectra of the mixtures of tetraisopentyl-1,2,3,4-butanetetracarboxylic esters have resonance signals in the range from 0.8 ppm to 1.0 ppm which are formed by the signals of the hydrogen atoms of the methyl group(s) of the isomeric pentyl substituents ($C14H_3$, $C231H_3$, $C24H_3$, $C33H_3$). The signals in the range of chemical shifts from 3.60 to 4.40 ppm may essentially be assigned to the hydrogen atoms of the methylene group adjacent to the oxygen in the alcohol radical ($C10H_2$, $C20H_2$, $C30H_2$). The protons on C20 are subject to a high-field shift due to the adjacent tertiary carbon atom and appear between 4.03 and 3.84 ppm while the protons on C10 and C30 give signals at lower shifts of 4.20 to 4.03 ppm and are mutually overlapping.

Quantification was effected by comparative determination of the area under the respective resonance signals, i.e. the area enclosed by the signal from the baseline. Commercial NMR software has program functions for integration of the signal area. In the present NMR spectroscopy study, the integration was conducted with the aid of the software TopSpin-Version 3.6.

To determine the mean degree of branching of the isomeric pentyl radicals in the mixture according to the invention, the integral value of the signals in the range from 0.68 to 1.11 ppm ($I(CH_3)$) is first divided by the integral value of the signals in the range from 3.60 to 4.40 ppm ($I(OCH_2)$). In this way, an intensity ratio which indicates the ratio of the number of hydrogen atoms present in a methyl group to the number of hydrogen atoms present in a methylene group adjacent to an oxygen is obtained. Since three hydrogen atoms per methyl group and two hydrogen atoms in every methylene group adjacent to an oxygen are present, the intensities have to be divided by 3 and 2 respectively to obtain the ratio of the number of methyl groups to the number of methylene groups adjacent to an oxygen in the pentyl radical. Since a linear n-pentyl radical having only one methyl group and one methylene group adjacent to an oxygen does not contain any branching and accordingly has to have a degree of branching of 0, it is necessary to subtract the value 1 from the ratio.

The mean degree of branching C6 can thus be calculated by the formula $$DB = \tfrac{2}{3} \cdot I(CH_3)/I(OCH_2) - 1$$

from the intensity ratio measured. In this formula, DB is the mean degree of branching, $I(CH_3)$ is the area integral assigned to the methyl hydrogen atoms, and $I(OCH_2)$ is the area integral of the methylene hydrogen atoms adjacent to the oxygen.

The product may contain 2-methylbutyl radicals and 3-methylbutyl radicals each having a degree of branching of 1, and also n-pentyl radicals having a degree of branching of 0, which means that the maximum mean degree of branching of any tetraisopentyl ester is always 1. From the deviation of the mean degree of branching from the value of 1, it is therefore possible to determine the molar proportion of n-pentyl radicals ($x_{pentyl}$) in the molecule.

$$x_{pentyl} = 1 - DB$$

The proportion of 2-methylbutyl radicals cannot be calculated using the integration of the baseline-separated signals in the range from 3.60 to 4.40 ppm.

Here too, the signals of the protons on C20 ($C^{20}H_2$, multiplet between 3.95 and 4.28 ppm) are separated from the signals of the protons on C10 and C30 ($C^{10}H_2$ and $C^{30}H_2$; multiplet between 4.29 and 4.55 ppm) in the minimum of the valley cut between the signal groups.

The molar proportion of 2-methylbutyl radicals ($x_{2\text{-}methylbutyl}$) can be calculated by the formula $$x_{2\text{-}methylbutyl} = I(OC^{19}H_2)/I(OCH_2)$$

by forming the ratio of the intensity of the signals for the $OC^{20}H_2$ protons ($I(OC^{20}H_2)$) to the intensity of all $OCH_2$ protons ($I(OCH_2)$).

The molar proportion of 3-methylbutyl radicals ($x_{3\text{-}methylbutyl}$) is thus calculated from the difference between the two previous molar proportions and 1.

$$x_{3\text{-}methylbutyl} = 1 - x_{2\text{-}methylbutyl} - x_{pentyl}$$

The aforementioned method made it possible to determine the proportions of the respective radicals in the samples (see table 1):

TABLE 1

| Composition of the ester mixtures by NMR analysis | | |
| --- | --- | --- |
| Proportion of 2-methylbutyl (product) [%] | Proportion of 3-methylbutyl (product) [%] | Proportion of n-pentyl (product) [%] |
| Ex. 1*    52.2 | 0 | 47.8 |
| Ex. 2*    59.5 | 0 | 40.5 |
| Ex. 3*    59.0 | 21.2 | 19.8 |
| Ex. 4*    45.3 | 0 | 54.7 |
| Comp. Ex. 5    39.2 | 0 | 60.8 |
| Comp. Ex. 6    0 | 0 | 100 |

*Inventive

The ester mixtures from table 2 were investigated in terms of application-relevant properties.

Measurement of Thickening Behaviour

PVC plastisols, as used for manufacturing topcoat films for example, were produced. The amounts in the plastisol formulations are each reported in parts by mass (phr). The formulation is reported in table 2.

TABLE 2

| Plastisol formulation | |
| --- | --- |
| | phr |
| PVC (Vestolit P1430 K70 - Ultra; from Vestolit) | 100 |
| Plasticizer or plasticizer mixture | 50 |
| Epoxidized soybean oil as co-stabilizer (Edenol D81, from Emery Oleochemicals) | 3 |
| Heat stabilizer based on Ba/Zn ((Reagens MBL 197/9PF, from Reagens) | 2 |

First the liquid constituents and then the pulverulent constituents were weighed out into a PE beaker. The mixture was stirred manually with a spatula in such a way that no unwetted powder remained present. The mixing beaker was then clamped into the clamping means of a dissolver stirrer, After switching on the stirrer, the speed was slowly increased to about 2000 rpm (revolutions per minute). During that time, the plastisol was carefully deaerated. To this end, the pressure was adjusted to a pressure below 20 mbar. As soon as the plastisol had reached a temperature of about 30° C., the speed was lowered to about 350 rpm. Henceforth, the plastisol was deaerated at that speed and a pressure below 20 mbar for 9 minutest. This ensured that there could be no premature partial gelation during homogenizing of the plastisol.

Measurement of the thickening behaviour in principle comprises measuring the viscosity of the produced plastisols at various times divided by the viscosity shortly after formulation. The viscosity of the plastisols produced in example 1) was measured with a Physica MCR 101 rheometer (from Anton Paar Germany GmbH) with the aid of the accompanying software, using the rotation mode and the CC27 measuring system. The measurement was conducted after the plastisols had been thermally equilibrated at 25° C. for 24 hours after their production.

The measurement involved the following points:
preliminary shear at 100 s$^{-1}$ for a period of 60 seconds, during which no measurements were taken downward shear rate ramp from 200 s$^{-1}$ to 0.1 s$^{-1}$·30 measurement points were recorded, each with a measurement point duration of 10 seconds.

The measurements were performed at room temperature after 2 hours, 24 hours and 7 days (in each case based on the time of production of the plastisols). The viscosity obtained at a shear rate of 0.1 s$^{-1}$, 1 s$^{-1}$ and 10 s$^{-1}$ was determined in each case. The results are shown in table 3.

The percentage increase in viscosity over time for the individual shear rates was determined as follows:

1 d=(viscosity after 24 hours-viscosity after 2 hours)/viscosity after 2 hours 7 d=(viscosity after 7 days-viscosity after 2 hours)/viscosity after 2 hours

TABLE 3

Thickening behaviour of the samples
Thickening behaviour of the tetraisopentyl esters of
butanetetracarboxylic acids at various shear rates

| | Shear rate | | | | | |
| | 0.1 s$^{-1}$ | | 1 s$^{-1}$ | | 10 s$^{-1}$ | |
| | Measurement time | | | | | |
| | 1 d | 7 d | 1 d | 7 d | 1 d | 7 d |
| Example 1* (52 mol % 2-MB) | 16.8 | 55.8 | 15.2 | 48.1 | 10.0 | 31.4 |
| Example 2* (59 mol % 2-MB) | 18.7 | 60.9 | 15.7 | 49.3 | 9.7 | 30.1 |
| Example 3* (59 mol % 2-MB, 21% Pe, 19% 3-MB) | 16.0 | 55.6 | 14.8 | 45.8 | 8.1 | 24.0 |
| Example 4 (45 mol % 2-MB)* | 15.8 | 54.1 | 13.4 | 45.5 | 9.1 | 30.4 |
| Comparative example 5 (39 mol % 2-MB) | 19.4 | 63.5 | 16.5 | 51.7 | 10.1 | 32.8 |
| Comparative example 6 (pure n-Pe) | 18.3 | 63.5 | 16.2 | 54.7 | 12.0 | 39.3 |

In summary it is apparent that the thickening behaviour in the claimed range is better than outside the claimed range. The increase in viscosity over time is less in the claimed ramie than in the comparative examples.

The invention claimed is:

1. A mixture, comprising:
tetraisopentyl esters of 1,2,3,4-butanetetracarboxylic acid,
wherein 45 to 60 mol % of isopentyl radicals in the mixture are 2-methylbutyl radicals.

2. The mixture according to claim 1, wherein 50 to 60 mol % of the isopentyl radicals in the mixture are 2-methylbutyl radicals.

3. The mixture according to claim 1, wherein 40 to 55 mol % of the isopentyl radicals in the mixture are n-pentyl radicals, 3-methylbutyl radicals, or a mixture of n-pentyl radicals and 3-methylbutyl radicals.

4. The mixture according to claim 2, wherein 40 to 50 mol % of the isopentyl radicals in the mixture are n-pentyl radicals, 3-methylbutyl radicals, or a mixture of n-pentyl radicals and 3-methylbutyl radicals.

5. A process for producing the mixture of tetraisopentyl esters of 1,2,3,4-butanetetracarboxylic acid according to claim 1, the process comprising:
producing the tetraisopentyl esters of 1,2,3,4-butanetetracarboxylic acid either
by esterification of the 1,2,3,4-butanetetracarboxylic acid with an isopentanol mixture, or by transesterification of a tetramethyl ester of the 1,2,3,4-butanetetracarboxylic acid with an isopentanol mixture.

6. The process according to claim 5, wherein water of reaction formed during the esterification is separated during the reaction.

7. The process according to claim 5, wherein the esterification is performed at a temperature in the range from 120° C. to 250° C.

8. A method, comprising:
mixing the mixture of tetraisopentyl esters of 1,2,3,4-butanetetracarboxylic acid according to claim 1, as a plasticizer, with at least one polymer.

9. A plasticizer composition, containing:
the mixture of tetraisopentyl esters of 1,2,3,4-butanetetracarboxylic acid according to claim 1, and
at least one further plasticizing compound.

10. The plasticizer composition according to claim 9, wherein the at least one further plasticizing compound is selected from the group consisting of adipates, benzoates, chlorinated hydrocarbons, citrates, cyclohexanedicarboxylates, epoxidized fatty acid esters, epoxidized vegetable oils, epoxidized acylated glycerides, furandicarboxylates, phosphates, succinates, sulfonamides, sulfonates, terephthalates, trimellitates, and oligomeric or polymeric esters based on adipic acid, succinic acid, or sebacic acid.

11. The plasticizer composition according to claim 9, wherein the plasticizer composition contains less than 5% by weight of phthalates.

12. A plastics composition, containing:
the mixture of tetraisopentyl esters of 1,2,3,4-butanetetracarboxylic acid according to claim 1, and
one or more polymers.

13. The plastics composition according to claim 12, wherein the one or more polymers are selected from the group consisting of PVC, homo- or copolymers based on ethylene, propylene, butadiene, vinyl acetate, glycidyl acrylate, glycidyl methacrylate, ethyl acrylate, butyl acrylate or methacrylate with alkoxy radicals of branched or unbranched alcohols having one to ten carbon atom(s), acrylonitrile or cyclic olefins, polyvinylidene chloride (PVDC), polyacrylates, polymethyl methacrylate (PMMA), polyalkyl methacrylate (PAMA), polyureas, silylated polymers, fluoropolymers, polyvinylidene fluoride (PVDF), polytetrafluoroethylene (PTFE), polyvinyl acetate (PVAc), polyvinyl alcohol (PVA), polyvinyl acetals, polyvinyl butyral (PVB), polystyrene polymers, polystyrene (PS), expandable polystyrene (EPS), acrylonitrile-styrene-acrylate (ASA), styrene-acrylonitrile (SAN), acrylonitrile-butadiene-styrene (ABS), styrene-maleic anhydride copolymer (SMA), styrene-methacrylic acid copolymer, polyolefins, polyethylene (PE), polypropylene (PP), thermoplastic polyolefins (TPO), polyethylene-vinyl acetate (EVA), polycarbonates, polyethylene terephthalate (PET), polybutylene terephthalate (PBT), polyoxymethylene (POM), polyimide (PA), polyethylene glycol (PEG), polyurethane (PU), thermoplastic polyurethane (TPU), polysulfides (PSu), biopolymers, polylactic acid (PLA), polyhydroxybutyral (PHB), polyhydroxyvaleric acid (PHV), polyesters, starch, cellulose and cellulose derivatives, nitrocellulose (NC), ethylcellulose (EC), cellulose acetate (CA), cellulose acetate/butyrate (CAB), rubber, and silicones.

14. The plastics composition according to claim 12, wherein an amount of the mixture of tetraisopentyl esters of 1,2,3,4-butanetetracarboxylic acid in the plastics composition is 5 to 150 parts by mass, per 100 parts by mass of the one or more polymers.

15. An article, comprising:

the plastics composition according to claim 12, wherein the article is selected from the group consisting of adhesives, sealing compositions, coating compositions, lacquers, paints, plastisols, foams, synthetic leathers, floor coverings, roofing membranes, underbody protection, fabric coatings, cables, wire insulation, hoses, extruded articles, films, automotive interiors, wallpapers, inks, toys, contact sheets, foodstuffs packaging, and medical articles.

16. The method according to claim 8, wherein the at least one polymer is PVC or a vinyl chloride-containing copolymer.

17. The plasticizer composition according to claim 11, wherein the plasticizer composition contains less than 0.1% by weight of the phthalates.

18. The plastics composition according to claim 14, wherein the amount of the mixture of tetraisopentyl esters of 1,2,3,4-butanetetracarboxylic acid in the plastics composition is 15 to 110 parts by mass, per 100 parts by mass of the one or more polymers.

* * * * *